US005661130A

United States Patent [19]
Meezan et al.

[11] Patent Number: 5,661,130
[45] Date of Patent: Aug. 26, 1997

[54] ABSORPTION ENHANCERS FOR DRUG ADMINISTRATION

[75] Inventors: Elias Meezan; Dennis J. Pillion, both of Birmingham, Ala.

[73] Assignee: The UAB Research Foundation, Birmingham, Ala.

[21] Appl. No.: 83,074

[22] Filed: Jun. 24, 1993

[51] Int. Cl.$^6$ .......................... C07G 3/00; A61K 31/70; A61K 38/00; A61K 38/28
[52] U.S. Cl. .................. 514/25; 514/24; 514/53; 514/54; 514/912; 514/2; 514/3; 514/8; 536/4.1; 536/115; 536/116; 536/118; 536/120; 536/122; 536/123.13
[58] Field of Search .......................... 536/4.1, 115, 116, 536/118, 120, 122, 123.13; 514/24, 25, 53, 54, 2, 3, 8, 912

[56] References Cited

U.S. PATENT DOCUMENTS

| | | | |
|---|---|---|---|
| 4,868,289 | 9/1989 | Magnusson et al. | 536/4.1 |
| 5,182,258 | 1/1993 | Chiou | 514/3 |
| 5,369,095 | 11/1994 | Kee et al. | 514/24 |

OTHER PUBLICATIONS

Masahiro Murakami et al., "Assessment of Enhancing Ability of Medium–Chain Alkyl Saccharides as New Absorption Enhancers in Rat Rectum," *International Journal of Pharmaceutics*, 79:159–169 (1992).

Lars Hovgaard et al., "Insulin Stabilization and GI Absorption," *Journal of Controlled Release*, 19:99–108 (1992).

Dennis J. Pillion et al., "Systemic Absorption of Insulin Delivered Topically to the Rat Eye," *Investigative Ophthalmology & Visual Science*, 32(12):3021–3027 (Nov. 1991).

Taro Ogiso et al., "Percutaneous Absorption of Elcatonin and Hypocalcemic Effect in Rat," *Chem. Pharm. Bull.*, 39(2):449–453 (1991).

Akira Yamamoto et al., "The Ocular Route for Systemic Insulin Delivery in the Albino Rabbit," *The Journal of Pharmacology and Experimental Therapeutics*, 249(1):249–255 (1989).

George C.Y. Chiou et al., "Systemic Delivery of Insulin Through Eyes to Lower the Glucose Concentration," *Journal of Ocular Pharmacology*, 5(1):81–91 (1989).

George C.Y. Chiou et al., "Improvement of Systemic Absorption of Insulin Through Eyes with Absorption Enhancers," *Journal of Pharmaceutical Sciences*, 78(10):815–818 (Oct. 1989).

G. S. Gordon et al., "Nasal Absorption of Insulin: Enhancement by Hydrophobic Bile Salts," *Proc. Natl. Acad. Sci, USA*, 82:7419–7423 (Nov. 1985).

Robert Salzman et al., "Intranasal Aerosolized Insulin," *The New England Journal of Medicine*, 312(17):1078–1084 (Apr. 25, 1985).

Alan C. Moses et al., "Insulin Administered Intranasally as an Insulin–Bite Salt Aerosol –Effectiveness and Reproducibility in Normal and Diabetic Subjects," *Diabetes*, 32:1040–1047 (Nov. 1983).

*Primary Examiner*—John Kight
*Assistant Examiner*—Everett White
*Attorney, Agent, or Firm*—Needle & Rosenberg, P.C.

[57] ABSTRACT

The present invention relates to a method of increasing the absorption of a compound via the ocular, nasal, nasolacrimal or inhalation route into the circulatory system of a patient. In particular, a method comprising administering with the compound an absorption enhancer comprising a nontoxic, nonionic alkyl glycoside is provided. Additionally provided are methods of raising or lowering the blood glucose level by administering glucagon or insulin, respectively, with such absorption enhancers. Finally, compositions for raising or lowering the blood glucose level are provided.

11 Claims, No Drawings

ABSORPTION ENHANCERS FOR DRUG ADMINISTRATION

BACKGROUND OF THE INVENTION

1. Field of the Invention

The present invention relates to a method of increasing the absorption of a compound via the ocular, nasal, nasolacrimal or inhalation route into the circulatory system of a patient. In particular, a method comprising administering with the compound an absorption enhancers comprising a nontoxic, nonionic alkyl glycoside is provided. Additionally provided are methods of raising or lowering the blood glucose level by administering glucagon or insulin, respectively, with such absorption enhancers. Finally, compositions for raising or lowering the blood glucose level are provided.

2. Background Art

The revolution in biotechnology has impacted on the pharmaceutical industry and on the practice of medicine by making available a variety of previously known and newly discovered proteins, e.g., insulin, growth hormone, interferons; peptides, e.g., cyclosporine, enkephalins and other synthetic peptides; as well as macromolecules, e.g., heparin and derivatives; drugs which open up an entirely new dimension to the treatment of disease. A serious limitation to the development and use of such agents, however, is the ability to deliver them safely and efficiently to their therapeutic site of action (Lee, V. H. L. et at., in "Peptide and Protein Drug Delivery," V. H. L. Lee ed. Marcel Dekker, New York, pp. 1–56 (1991)). Because these drugs are usually available in only small amounts, are expensive and are biologically fragile—subject to denaturation and degradation—a rapid and efficient route of delivery is an important requirement for their successful use in therapy. Unfortunately, for the most part, the practical delivery of such agents has been limited to injectable routes such as intravenous, intramuscular and subcutaneous administration. Insulin is the classic example of such an agent whose obligatory use in insulin-dependent diabetes mellitus requires administration via injection. In the case of other established macromolecular drugs, such as heparin, the requirement for delivery by injection and the availability of alternative, but far from ideal agents, such as the oral anticoagulants, has restricted the use of the injectable agent to the clinic or hospital, thus denying its benefits to a large outpatient population. Although many attempts have been made to safely and efficiently administer insulin, heparin and other macromolecular drugs by non-injectable routes, none have proved successful, and it has become apparent that the success of such attempts depends on the discovery of a safe and efficient agent to enhance absorption of the macromolecules (see Lee et at.).

Buccal absorption of insulin is minimal in the absence of a surfactant agent, but it has been shown to be improved with penetration-enhancers such as glycocholate and Brij 35. However, the low bioavailabilty observed and the possible toxicity of the enhancing agents used previously have made this route impractical (Oh, C. K. et at, *Meth. Find. Exp. Clin. Pharmacol.*, 12:205–212 (1990)). Similar findings have been reported for insulin absorption across the rectal mucosa (Rytting, J. H. et al., (V. H. L. Lee, ed.) Marcel Dekker, New York pp. 579–594 (1991)). However, it has recently been reported that dodecylmaltoside was effective in promoting the absorption of high molecular weight sugar compounds, such as dextrans, and other molecules, such as carboxyfluoroscein, across the rectal mucosa of rats without producing any apparent histological change to the tissue (Murakami, M. et al., *Int. J. Pharm.*, 79:159–169 (1992)). Hovgaard et al., (*J. Controlled Release*, 19:99–108 (1992)) reported the use of high concentrations of dodecyl maltoside to increase the absorption of insulin across the rectal mucosa in rats. High concentrations were found to be necessary for rectal absorption (3.2%–12.8% dodecyl maltoside). It was concluded by Hovgaard et al. that rectal absorption enhancers function at least in part because they render the insulin-enhancer complex more resistant to enzymatic degradation by intestinal digestive enzymes. The use of dodecyl maltoside in the reported concentrations would be too irritating and toxic to the much more sensitive ocular and nasal mucosa and thus unsuitable for ocular and nasal absorption enhancers.

A synthetic analogue of calcitonin, a hypocalcemic peptide has been shown to be effectively absorbed percutaneously in the rat by applying it in transdermal dosage form as a gel containing a combination of bile salts and the alkyl glycosides octylglucoside or octylthioglucoside (Ogiso, T. et al., *Chem. Pharm. Bull.*, 39:449–453 (1991)).

We had previously shown that systemic delivery of insulin via the ocular and nasal-lacrimal route in amounts sufficient to lower blood sugar in experimentally diabetic rats was made possible by including 1% saponin in the eye drops with the insulin (Pillion, D. J. et al., *Invest. Ophthalmol. Vis. Sci.*, 32:3021–3027 (1991)). However, saponins, which have also been used by others to promote ocular absorption of insulin (Chiou, G. C. Y. et al., *J. Pharm. Sci.*, 78:815–818 (1989); Chiou, C. Y. et al., *J. Ocular Pharmacol.* 5:81–91 (1989); U.S. Pat. No. 5,182,258 (Chiou et al.), are a large and complex class of compounds, derived from plants, which are difficult to prepare in pure form and have deleterious properties such as being irritants (Price, K. R. et al., *CRC Crit. Rev. Food Sci. Nutr.*, 26:27–135 (1987)). Another surfactant, Tween 20, which has the same 12 carbon alkyl side chain as dodecylmaltoside, but which has a polyoxyethylene moiety in place of maltose, has been reported to be almost without effect in allowing absorption of insulin in rabbit eyes (Chiou, et al., *J. Pharm. Sci.*,) Furthermore, saponin, fusidic acid, EDTA, polyoxyethylene-9-lauryl ether, glycocholate, taurocholate, deoxycholate and decamethonium as ocular absorption enhancers have met with limited success in promoting the ocular absorption of insulin (Pillion et al., Chiou et al., (*J. Pharm. Sci.*), Chiou et al. (*J. Ocular Pharmacol.*) and Yamamoto et al., *J. Pharmacol. Exptl. Ther.*, 249:249–255 (1989)), but the toxicity of these agents makes their therapeutic usage problematic.

Intranasal administration of insulin in the form of a nasal spray with bile salts or laureth-9 as absorption enhancers has been tested in clinical trials with normal and diabetic subjects, but also with only limited success (Moses, A. C. et al., *Diabetes*, 32:1040–1047 (1983); Gordon, G. S. et al., *Proc. Natl. Acad. Sci. USA*, 82:7419–7423 (1985); Salzmann, R. et al., *New Engl. J. Med.*, 312:1078–1084 (1985)). The major limiting factors which have prevented the practical development of this route for general use is the low efficiency of absorption across the nasal mucosa and the local and systemic toxicity of the penetration-enhancing agents used (Moses et al., Gordon et al., Salzmann et al and Chadwick, U.S. et al., *Gut*, 17:10–17 (1976)). Aerosolized insulin has been absorbed via the respiratory route, but only at low efficiency, probably because no absorption enhancer was employed (Wigley, F. M. et al., *Diabetes*, 20:552–556 (1971).

Dodecylmaltoside and other alkyl glycosides can readily be obtained in pure form and have well defined, simple structures (Neugebauer, J., "A Guide to the Properties and Uses of Detergents in Biology and Biochemistry," Calbiochem Corporation (1988)). They are mild nonionic surfactants which have generally been shown to be nontoxic to several different cell types (DiCorleto, P. E. et al., *J. Immunol.*, 143:3666–3672 (1989) and LeGrue, S. J. et al., *J. Natl. Cancer Inst.*, 69:131–136 (1982)). Octylglucoside had no effect on the viability or morphology of monocytes or endothelial cells (DiCorleto et al.) and was non-cytolytic to intact mouse fibrosarcoma cells (LeGrue et al.) Orally administered alkyl glycosides, including octyl β-D-glucoside and dodecyl β-D-maltoside, have also been shown to be metabolized to nontoxic metabolites by cleavage to sugars and long chain alcohols which enter into the pathways of carbohydrate and lipid metabolism. It was suggested that these compounds would be suitable for use as food additives because of their lack of toxicity (Weber, N. et al., *J. Nutr.*, 114:247–254 (1984)). In contrast, other agents which have been shown to enhance the systemic absorption of insulin, such as bile salts or laureth-9, are known to be irritating to mucosal surfaces and are not metabolized to simple products in the body (Moses et al., Gordon et al., and Salzmann et al.). In the case of bile salts, it is known that they are toxic to the gastrointestinal mucosa when administered orally and that they cause ultrastructural abnormalities of the nasal mucosa when used to administer insulin by this route (Moses et al., Gordon et al., and Chadwick et al.).

Thus, many attempts have been unsuccessfully made to obtain a suitable, effective absorption enhancer for drugs, and there is a great need for such an enhancer. The ideal absorption or penetration enhancer would preserve the biological activity of the protein or other drug and thus should be nonreactive and non-denaturing. It should enhance the passage of the drug through membrane barriers without damaging the structural integrity and biological functions of the membrane. Most importantly, both it and its metabolites should be nonirritating and nontoxic, both at the site of application, and also systemically, since it is likely that any enhancer of drug absorption will itself be absorbed and have to be metabolized and/or cleared from the body. Such an absorption enhancer is provided herein.

SUMMARY OF THE INVENTION

The present invention relates to a method of increasing absorption of a compound into the circulatory system of a subject comprising administering via the ocular, nasal, nasolacrimal, or inhalation route the compound and an absorption increasing mount of a suitable nontoxic, nonionic glycoside having a hydrophobic alkyl joined by a linkage to a hydrophilic saccharide.

The present invention also relates to a method of lowering blood glucose level in a subject comprising administering via the ocular, nasal, nasolacrimal or inhalation route, a blood glucose-reducing amount of a composition comprising insulin and an absorption increasing amount of a suitable nontoxic, nonionic alkyl glycoside having a hydrophobic alkyl joined by a linkage to a hydrophilic saccharide, thereby increasing the absorption of insulin and lowering the level of blood glucose.

The instant invention further relates to a method of raising blood glucose level in a subject comprising administering via the ocular, nasal, nasolacrimal or inhalation route a blood glucose-raising amount of a suitable composition comprising glucagon and an absorption increasing amount of a suitable nontoxic, nonionic alkyl glycoside having a hydrophobic alkyl joined by a linkage to a hydrophilic saccharide, thereby increasing the absorption of glucagon and raising the level of blood glucose.

The present invention also relates to a composition comprising (a) a nontoxic, nonionic alkyl glycoside having a hydrophobic alkyl joined by a linkage to a hydrophilic saccharide, in concentration in the range of 0.01% to 1.0%, capable of increasing absorption of a compound into the circulatory system of a patient and (b) an agent selected from the group consisting of insulin and glucagon.

Accordingly, it is an object of the present invention to provide a method of increasing the absorption of a compound into the circulatory system of a subject by utilizing the ocular, nasal and nasolacrimal or inhalation route.

Another object of the present invention is to provide compositions and methods for raising or lowering the blood glucose level in a subject utilizing the provided method for increasing absorption of compounds, and thus treating hypoglycemia or diabetes mellitus, respectively.

Finally, an object of the present invention is to provide compositions for raising and lowering blood glucose levels.

DETAILED DESCRIPTION OF THE INVENTION

The present invention may be understood more readily by reference to the following detailed description of specific embodiments and the Examples included therein.

The present invention provides a method of increasing absorption of a compound into the circulatory system of a subject comprising administering via the ocular, nasal, nasolacrimal, or inhalation route the compound and an absorption increasing amount of a suitable nontoxic, nonionic alkyl glycoside having a hydrophobic alkyl joined by a linkage to a hydrophilic saccharide. The compound and the alkyl glycoside can be mixed prior to administration, or they can be administered sequentially, in either order. It is preferred that they be mixed prior to administration.

As used in the claims, "a" can mean one or more.

As used herein, "hypoglycemia" means a hypoglycemic crisis.

"Nontoxic," as used herein, means that the alkyl glycoside molecule has a sufficiently low toxicity to be suitable for human administration. Preferred alkyl glycosides are non-irritating to the tissues to which they are applied. Any alkyl glycoside should be of minimal or nontoxicity to the cell, such as not to cause damage to the cell. Toxicity for any given alkyl glycoside may vary with the concentration of alkyl glycoside used. It is also beneficial if the alkyl glycoside chosen is metabolized or eliminated by the body and if this metabolism or elimination is done in a manner that will not be harmfully toxic.

As used herein, "alkyl glycoside" refers to any sugar joined by a linkage to any hydrophobic alkyl, as is known in the art. The hydrophobic alkyl can be chosen of any desired size, depending on the hydrophobicity desired and the hydrophilicity of the saccharide moiety. A preferred range of alkyl chains is from 9 to 24 carbon atoms. An even more preferred range is from 9 to 14 carbon atoms.

As used herein; "saccharide" is inclusive of monosaccharides, oligosaccharides or polysaccharides in straight chain or ring forms. Oligosaccharides are saccharides having two or more monosaccharide residues.

As used herein, a "suitable" alkyl glycoside means one that fulfills the limiting characteristics of the invention, i.e., that the alkyl glycoside be nontoxic and nonionic, and that it increases the absorption of a compound when it is administered with the compound via the ocular, nasal, nasolacrimal or inhalation route. Suitable compounds can be determined using the methods set forth in the examples.

Also as used herein, "hydrophile-lipophile balance number" (HLB) is a characteristic of individual surfactants that can be either calculated or determined empirically, as previously described (Schick, M. J. *Nonionic Surfactants*, p. 607 (New York: Marcel Dekker, Inc. (1967)). HLB can be calculated by the formula: 20×MW hydrophilic component/ (MW hydrophobic component+MW hydrophilic component), where MW=molecular weight (Rosen, M. J., *Surfactants and Interfacial Phenomena*, pp. 242–245, John Wiley, New York (1978)). The HLB is a direct expression of the hydrophilic character of the surfactant, i.e., the larger the HLB, the more hydrophilic the compound. A preferred surfactant has an HLB of from 10 to 20 and an even more preferred range of from 11 to 15.

Compounds whose absorption can be increased by the method of this invention include any compounds now known or later discovered, in particular drugs that are difficult to administer by other methods, for example, drugs that are degraded in the gastrointestinal (GI) tract or that are not absorbed well from the GI tract, or drugs that subjects could administer to themselves more readily via the ocular, nasal, nasolacrimal or inhalation route than by traditional self-administration methods such as injection. Some specific examples include peptides, polypeptides, proteins and other macromolecules, for example, peptide hormones, such as insulin and calcitonin, enkephalins, glucagon and hypoglycemic agents, such as tolbutamide and glyburide, and agents which are poorly absorbed by enteral routes, such as griseofulvin, an antifungal agent.

The saccharide can be chosen, for example, from any currently commercially available saccharide species or can be synthesized. The saccharide can be a monosaccharide, a disaccharide, an oligosaccharide or a polysaccharide, or a combination thereof to form a saccharide chain. Some examples of the many possible saccharides to use include glucose, maltose, maltotriose, maltotetraose, sucrose and trehalose. Preferable saccharides include maltose, sucrose and glucose.

Additionally, various oxygen atoms within the compounds can be substituted for by sulfur in order to decrease susceptibility to hydrolytic cleavage by glycohydrolases in the body (Defaye, J. and Gelas, J. in *Studies in Natural Product Chemistry* (Atta-ur-Rahman, ed.) Vol. 8, pp. 315–357, Elsevier, Amsterdam, 1991). For example, the heteroatom of the sugar ring can be either oxygen or sulfur, or the linkage between monosaccharides in an oligosaccharide can be oxygen or sulfur (Horton, D. and Wander, J. D., "Thio Sugars and Derivatives," *The Carbohydrates: Chemistry and Biochemistry*, 2d. Ed. Vol. IB, (W. Reyman and D. Horton eds.), pp. 799–842, (Academic Press, New York), (1972)). Oligosaccharides can have either $\alpha$ (alpha) or $\beta$ (beta) anomeric configuration (see Pacsu, E., et al. in *Methods in Carbohydrate Chemistry* (R. L. Whistler, et al., eds.) Vol. 2, pp. 376–385, Academic Press, New York 1963).

Many alkyl glycosides can be synthesized by known procedures, i.e., chemically, as described, e.g., in Rosevear et al., *Biochemistry* 19:4108–4115 (1980) or Koeltzow and Urfer, *J. Am. Oil Chem. Soc.*, 61:1651–1655 (1984), U.S. Pat. No. 3,219,656 and U.S. Pat. No. 3,839,318 or enzymatically, as described, e.g., in Li et al., *J. Biol. Chem.*, 266:10723–10726 (1991) or Gopalan et al., *J. Biol. Chem.* 267:9629–9638 (1992).

The linkage between the hydrophobic alkyl and the hydrophilic saccharide can include, among other possibilities, a glycosidic, thioglycosidic (Horton), amide (*Carbohydrates as Organic Raw Materials*, F. W. Lichtenthaler ed., VCH Publishers, New York, 1991), ureide (Austrian Pat. 386,414 (1988); Chem. Abstr. 110:137536p (1989); see Gruber, H. and Greber, G., "Reactive Sucrose Derivatives" in *Carbohydrates as Organic Raw Materials*, pp. 95–116) or ester linkage (Sugar Esters: *Preparation and Application*, J. C. Colbert ed., (Noyes Data Corp., New Jersey), (1974)).

Examples from which useful alkyl glycosides can be chosen for the therapeutic composition include: alkyl glycosides, such as octyl-, nonyl-, decyl-, undecyl-, dodecyl-, tridecyl-, tetradecyl, pentadecyl-, and octadecyl $\alpha$- or $\beta$-D-maltoside, -glucoside or -sucroside (synthesized according to Koeltzow and Urfer; Anatrace Inc., Maumee, Ohio; Calbiochem, San Diego, Calif.; Fluka Chemie, Switzerland); alkyl thiomaltosides, such as heptyl, octyl, dodecyl-, tridecyl-, and tetradecyl-$\beta$-D-thiomaltoside (synthesized according to Defaye, J. and Pederson, C., "Hydrogen Fluoride, Solvent and Reagent for Carbohydrate Conversion Technology" in *Carbohydrates as Organic Raw Materials*, 247–265 (F. W. Lichtenthaler, ed.) VCH Publishers, New York (1991); Ferenci, T., *J. Bacteriol*, 144:7–11 (1980)); alkyl thioglucosides, such as heptyl- or octyl 1-thio $\alpha$- or $\beta$-D-glucopyranoside (Anatrace, Inc., Maumee, Ohio; see Saito, S. and Tsuchiya, T. *Chem. Pharm. Bull.* 33:503–508 (1985)); alkyl thiosucroses (synthesized according to, for example, Binder, T. P. and Robyt, J. F., Carbohydr. Res. 140:9–20 (1985)); alkyl maltotriosides (synthesized according to Koeltzow and Urfer); long chain aliphatic carbonic acid amides of sucrose $\beta$-amino-alkyl ethers; (synthesized according to Austrian Patent 382,381 (1987); *Chem. Abstr.*, 108:114719 (1988) and Gruber and Greber pp. 95–116); derivatives of palatinose and isomaltamine linked by amide linkage to an alkyl chain (synthesized according to Kunz, M., "Sucrose-based Hydrophilic Building Blocks as Intermediates for the Synthesis of Surfactants and Polymers" in *Carbohydrates as Organic Raw Materials*, 127–153); derivatives of isomaltamine linked by urea to an alkyl chain (synthesized according to Kunz); long chain aliphatic carbonic acid ureides of sucrose $\beta$-amino-alkyl ethers (synthesized according to Gruber and Greber, pp. 95–116); and long chain aliphatic carbonic acid amides of sucrose $\beta$-amino-alkyl ethers (synthesized according to Austrian Patent 382,381 (1987), *Chem. Abstr.*, 108:114719 (1988) and Gruber and Greber, pp. 95–116).

Some preferred glycosides include maltose, sucrose, and glucose linked by glycosidic linkage to an alkyl chain of 9, 10, 12 or 14 carbon atoms, i.e., nonyl-, decyl-, dodecyl- and tetradecyl sucroside, glucoside, and maltoside. These compositions are nontoxic, since they are degraded to an alcohol and an oligosaccharide, and amphipathic.

The above examples are illustrative of the types of glycosides to be used in the methods claimed herein; the list is not exhaustive. Derivatives of the above compounds which fit the criteria of the claims should also be considered when choosing a glycoside. All of the compounds can be screened for efficacy following the methods taught in the examples.

Preferred concentrations of alkyl glycosides are those within the range of 0.01–1%, as such low concentrations reduce any potential irritability or damage to the tissues while still increasing absorption. Even more preferred are concentrations within the range of 0.125–0.5%. From a medical standpoint, the less absorption enhancer used, that is still as effective as desired, the better for the subject.

The method of this invention can also include the administration, along with the alkyl glycoside and a protein or peptide, a protease or peptidase inhibitor, such as aprotinin, bestatin, alpha$_1$ proteinase inhibitor, recombinant secretory leucocyte protease inhibitor, captopril and other angiotensin converting enzyme (ACE) inhibitors and thiorphan, to aid the protein or peptide in reaching its site of activity in the body in an active state (i.e., with degradation minimal enough that the protein is still able to function properly). The protease or peptidase inhibitor can be mixed with the alkyl glycoside and compound and then administered, or it can be administered separately, either prior to or after administration of the glycoside and compound.

The amount of compound administered will, of course, be dependent on the subject being treated, the subject's weight, the severity of symptoms and the judgment of the prescribing physician. Generally, however, dosage will approximate that which is typical for known methods of administration of the specific compound. For example, for intranasal administration of insulin, an approximate dosage would be about 0.5 unit/kg regular porcine insulin (Moses et al.). Dosage for compounds affecting blood glucose levels optimally would be that required to achieve proper glucose levels, for example, to a normal range of about 5–6.7 mM. Additionally, an appropriate amount may be determined by one of ordinary skill in the art using only routine testing given the teachings herein (see Examples).

The compound can be administered in a format selected from the group consisting of a drop, a spray, an aerosol and a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (Ocusert, Alza Corp., California; Joshi, A., S. Ping and K. J. Himmelstein, Patent Application WO 91/19481). These systems maintain prolonged drug contact with the absorptive surface preventing washout and nonproductive drug loss.

Also provided is a method of lowering blood glucose level in a subject comprising administering via the ocular, nasal, nasolacrimal or inhalation route, a blood glucose-reducing amount of a composition comprising insulin and an absorption increasing amount of a suitable nontoxic, nonionic alkyl glycoside having a hydrophobic alkyl joined by a linkage to a hydrophilic saccharide, thereby increasing the absorption of insulin and lowering the level of blood glucose. A "blood glucose-reducing amount" of such a composition is that amount capable of producing the effect of reducing blood glucose levels, as taught herein. Preferred is an amount that decreases blood glucose to normoglycemic or near normoglycemic range. Also preferred is an amount that causes a sustained reduction in blood glucose levels. Even more preferred is an amount sufficient to treat diabetes mellitus by lowering blood glucose level. Thus, the instant method can be used to treat diabetes mellitus. Preferred alkyl glycosides are the same as those described above and exemplified in the Examples.

Also provided is a method of raising blood glucose level in a subject comprising administering via the ocular, nasal, nasolacrimal or inhalation route a blood glucose-raising amount of a suitable composition comprising glucagon and an absorption increasing amount of a suitable nontoxic, nonionic alkyl glycoside having a hydrophobic alkyl joined by a linkage to a hydrophilic saccharide, thereby increasing the absorption of glucagon and raising the level of blood glucose. A "blood glucose-raising amount" of such a composition is that amount capable of producing the effect of raising blood glucose levels. Preferred is an amount that increases blood glucose to normoglycemic or near-normoglycemic range. Also preferred is an amount that causes a sustained raising of blood glucose levels. Even more preferred is an amount sufficient to treat hypoglycemia by raising blood glucose level. Thus this method can be used to treat hypoglycemia. Preferred alkyl glycosides are the same as those described above and exemplified in the Examples.

Also provided is a composition comprising (a) a nontoxic, nonionic alkyl glycoside having a hydrophobic alkyl joined by a linkage to a hydrophilic saccharide, in concentration in the range of 0.01% to 1.0%, capable of increasing absorption of a compound into the circulatory system of a patient and (b) an agent selected from the group consisting of insulin and glucagon. When this composition includes insulin, it can be used to cause the known effect of insulin in the bloodstream, i.e., lower the blood glucose levels in a subject, by administering it by, for example, the administration means of this invention, i.e., via the ocular, nasal, nasolacrimal or inhalation route. Such administration can be used to treat diabetes mellitus, using the concentrations of insulin known to those of skill in the art to properly lower blood glucose.

Similarly, when this composition includes glucagon, it can be used to cause the known effect of glucagon in the bloodstream, i.e., to raise the blood glucose levels in a subject. Such administration can therefore be used to treat hypoglycemia, including hypoglycemic crisis.

The present invention is more particularly described in the following examples which are intended as illustrative only since numerous modifications and variations therein will be apparent to those skilled in the art.

EXAMPLES

Hypoglycemic Effects of Insulin Delivered by the Ocular Route

All of the experimental results described were obtained in normal rats in which blood glucose values have been elevated as a consequence of anesthesia produced by xylazine/ketamine. This mimics the hyperglycemic state seen in diabetic animals and humans. The elevated levels of D-glucose that occur in response to anesthesia provide an optimal system in which to measure any systemic hypoglycemic action of insulin-containing eye drops. Hence, anesthetized rats given eye drops containing insulin can be compared to anesthetized animals given eye drops without insulin, and the differential systemic responses should accurately reflect the effect of insulin absorbed via the ocular route of administration.

Adult male Sprague-Dawley rats (250–350g) were fed ad libitum, and experiments were conducted between 10:00 a.m. and 3:00 p.m. Rats were anesthetized with a mixture of xylazine (7.5 mg/kg) and ketamine (50 mg/kg) given intraperitoneally (IP) and allowed to stabilize for 50–90 min before the administration of eye drops. Anesthesia of a normal rat with xylazine/ketamine produces an elevation in blood glucose values which provides an optimal state to determine the systemic hypoglycemic action of insulin-containing eye drops. Blood D-glucose values were measured by collecting a drop of blood from the tail vein at 5–10 min intervals throughout the experiment and applying the blood to glucometer strips (Chemstrip bG) according to directions provided with the instrument (Accu-Chek II, Boehringer Mannheim Diagnostics; Indianapolis, Ind.). Blood D-glucose values ranged from 200 to 400 mg/dl in anesthetized nondiabetic rats.

At time 0, after a 50–90 min stabilization period, rats were given 20 μl of eye drops composed of phosphate-buffered saline with or without 0.2% regular porcine insulin and 0.125–0.5% of the absorption enhancer to be tested. Eye drops were instilled at time 0 using a plastic disposable pipette tip with the eyes held open, and the rat was kept in a horizontal position on a warming pad (37° C.) throughout the protocol. The rats were given additional anesthesia if they showed signs of awakening. Rats received in each eye 20 μl of 0.125–0.5% absorption enhancer in phosphate buffered saline, pH 7.4 with (experimental) or without (control) 0.2% (50 U/ml) regular porcine insulin (Squibb-Novo, Inc.) for a total of 2 U per animal. Octyl β-D-maltoside, decyl-β-D-maltoside, dodecyl-β-D-maltoside, tridecyl-β-D-maltoside and tetradecyl-β-D-maltoside were obtained from Anatrace, Inc. (Maumee, Ohio). Hexylglucopyranoside, heptylglucopyranoside, nonylglucopyranoside, decylsucrose and dodecylsucrose were obtained from Calbiochem, Inc. (San Diego, Calif.); Saponin, BL-9 and Brij 78 were obtained from Sigma Chemical Co. (St. Louis, Mo.).

When rats received eye drops containing saline only, 0.2% regular porcine insulin in saline only, or absorption enhancer only, the level of D-glucose in the blood remained elevated. However, when rats received eye drops containing 0.2% regular porcine insulin and several alkylmaltoside or alkylsucrose compounds, a pronounced decrease in blood D-glucose values occurred and was maintained for up to two hours. Insulin administered ocularly with 0.5% dodecyl-β-D-maltoside (see Table 1) or 0.5% decyl-β-D-maltoside (see Table 3) results in a prompt and sustained fall in blood glucose levels which are maintained in the normoglycemic (80–120 mg/dl) or near-normoglycemic (120–160 mg/dl) range for the two hour duration of the experiment. Therefore, two alkylmaltosides are effective in achieving sufficient absorption of insulin delivered via the ocular route to produce a prompt and sustained fall in blood glucose levels in experimentally hyperglycemic animals. These agents, therefore, can be useful to achieve systemic absorption of insulin and other peptide, protein, e.g., glucagon and macromolecular drugs, e.g., heparin delivered via the ocular route in the form of eye drops.

Several other alkylmaltosides also proved effective as absorption enhancers for ocular administration of insulin including 0.5% tridecylmaltoside (see Table 3) and 0.125% (Table 2) and 0.5% tetradecyl maltoside. Based on these studies it appears that alkylmaltosides with the longer alkyl chains, i.e., dodecyl-, tridecyl- and tetradecyl-β-D-maltosides, and hence, with the greater hydrophobic/hydrophilic structural balance are more effective as absorption enhancers than those with shorter alkyl chains which produce less, e.g., decylmaltoside, or no, e.g., octylmaltoside, activity. It should be noted that the most effective alkylmaltosides produce effects comparable to or greater than those seen with other absorption enhancers such as saponin, with the added advantage that they can be metabolized to nontoxic products following systemic absorption.

The effects of the alkylmaltosides as absorption enhancers are dose-dependent, as can be seen by examining the effects of different concentrations ranging from 0.125–0.5% in producing a hypoglycemic effect when combined with insulin. Whereas, 0.5% and 0.375% dodecylmaltoside appear equally effective in achieving systemic absorption of insulin and reduction of blood glucose levels, 0.25% has a smaller and more transient effect and 0.125% is ineffective (Table 1). Similarly, tridecylmaltoside also shows a dose-dependent effect in lowering blood glucose concentrations when combined with insulin, but the effect achieved with even 0.25% of the enhancer is sustained for the two hour time course of the experiment. The dose-dependent effects of the alkylmaltosides suggest that they achieve enhancement of protein absorption via the ocular route in a graded fashion proportional to the concentration of the agent.

TABLE 1

Effect of Eye Drops Containing Insulin Plus Various Concentrations of Dodecyl Maltoside on Blood Glucose Values (in mg/dl) in Rat

| | Dodecyl Maltoside Concentration | | | |
|---|---|---|---|---|
| | .125% | .25% | .375% | .50% |
| Time (min) | Blood Glucose Concentrations (mg/dl) | | | |
| −20 | 305 ± 60 | 271 ± 38 | 305 ± 51 | 375 ± 9 |
| −10 | 333 ± 58 | 295 ± 32 | 308 ± 27 | 366 ± 12 |
| 0 | 338 ± 67 | 323 ± 62 | 309 ± 32 | 379 ± 4 |
| 30 | 349 ± 64 | 250 ± 48 | 212 ± 18 | 297 ± 18 |
| 60 | 318 ± 38 | 168 ± 22 | 134 ± 4 | 188 ± 25 |
| 90 | 325 ± 57 | 188 ± 55 | 125 ± 12 | 141 ± 13 |
| 120 | 342 ± 78 | 206 ± 63 | 119 ± 19 | 123 ± 5 |

The absorption enhancing effects of the alkyl saccharides are not confined to the alkylmaltosides alone since dodecylsucrose (0.125%, 0.25%, 0.375%) also shows a dose-dependent effect in producing ocular absorption of insulin and hence a reduction in blood glucose levels, even at 0.125% (from 335 mg/dl±26 mg/dl at time 0 min. to 150 mg/dl±44 mg/dl at time 120 min.). 0.5% decylsucrose was also effective in reducing blood glucose levels, but as shown for the alkylmaltosides, a reduction in the length of the alkyl chain, and hence the hydrophobic properties of the molecule, appears to reduce the potency of the alkylsucrose compounds. However, a significant and sustained reduction in blood glucose levels is achieved with 0.5% decylsucrose (from 313 mg/dl±15 mg/dl at time 0 min. to 164 mg/dl±51 mg/dl at time 120 min.). The absorption enhancing abilities of alkylsaccharides with two distinct disaccharide moieties suggests that it is the physicochemical properties of the compounds which are crucial to their activity and that other alkylsaccharides, e.g., dodecyllactose, have the right balance of properties to be equally or more effective as absorption enhancers while retaining the metabolic and nontoxic properties of the alkylsaccharide enhancing agents.

Studies with alkylglucosides were also conducted; 0.5% hexylglucoside and 0.5% heptylglucoside were ineffective at promoting insulin absorption from the eye, but 0.5% nonylglucoside effectively stimulated insulin absorption and reduced blood glucose levels (from 297 mg/dl to 150 mg/dl). This result once again showed that the alkyl chain length, as well as the carbohydrate moiety, play critical roles in effectively enhancing insulin absorption.

It should be noted that no damaging effects to the ocular surface were observed with any of the alkylmaltoside or alkylsucrose agents employed in these studies. Furthermore, the prompt and sustained hypoglycemic effects produced by these agents in combination with insulin suggest that these absorption enhancers do not adversely affect the biological activity of the hormone, in keeping with their nondenaturing, mild surfactant properties. Finally, since we have observed previously with other absorption enhancers that insulin administration via eye drops results in significant absorption of the hormone via the nasolacrimal drainage system, therapeutically effective administration of insulin with alkylmaltosides, alkylsucrose and like agents by intranasal administration was tested.

Hypoglycemic Effects of Insulin Delivered Intranasally

Tetradecylmaltoside in combination with insulin also produced a drop in blood D-glucose levels when administered in the form of a drop intranasally as well as via a drop by the ocular route. A rat administered eyedrops containing 0.2% regular porcine insulin with 0.125% tetradecylmaltoside produced a prompt and prominent drop in blood glucose levels which were then further decreased by administration of a nose drop containing the same concentration of insulin with 0.5% tetradecylmaltoside (Table 2). The protocol of the experiment was the same as described for ocular administration.

TABLE 2

Effect of Insulin Eye Drops, Containing 0.125% Tetradecyl Maltoside and Nose Drops Containing 0.5% Tetradecyl Maltoside on Blood Glucose Values in Rats

| Time (min) | Blood Glucose (mg/dl) |
|---|---|
| −20 | 319 |
| −10 | 311 |
| Eye drops added | |
| 0 | 322 |
| 15 | 335 |
| 30 | 276 |
| 45 | 221 |
| 60 | 212 |
| 75 | 167 |
| 90 | 174 |
| 105 | 167 |
| 120 | 208 |
| Nose Drops added | |
| 135 | 129 |
| 150 | 74 |
| 165 | 76 |
| 180 | 68 |

Hyperglycemic Effects of Glucagon Delivered by the Ocular Route

Our previous studies demonstrated that insulin absorption from the eye was stimulated by saponin, BL-9 and Brij-78; the latter two reagents were ineffective at stimulating the absorption of glucagon from the eye, whereas saponin was effective. Glucagon absorption from the eye was measured in rats given eye drops containing various surfactants plus glucagon (30 μg) (Eli Lilly, Indianapolis, Ind.) by monitoring an elevation in blood D-glucose levels. In these experiments, rats were anesthetized with sodium pentobarbital rather than xylazine/ketamine; this modification of the procedure resulted in basal blood glucose levels in the normoglycemic range and made it possible to readily monitor the hyperglycemic action of any glucagon absorbed from the eye. Once again, paired animals that received eye drops containing the surfactant agents only, or glucagon only, could be compared to animals receiving eye drops with surfactant agents and glucagon. When eyedrops containing 0.5% saponin plus glucagon were administered to rats, the level of D-glucose in blood rose significantly, but no such effect was observed with eye drops containing 0.5% BL-9 or 0.5% Brij-78 plus glucagon. Interestingly, when eye drops containing dodecylsucrose, decylmaltose or tridecylmaltose plus glucagon were administered to rats which had previously been treated with eyedrops containing these surfactant agents plus insulin, the glucagon was absorbed and blood D-glucose values were significantly increased (Table 3). This result confirms that certain alkylsaccharides can stimulate glucagon absorption from the eye, just as they stimulate insulin absorption. Additionally, the use of glucagon eyedrops to treat a hypoglycemic crisis is now possible provided that an appropriate surfactant agent is included in the eye drop formulation.

TABLE 3

Effect of Eye Drops Containing Insulin or Glucagon and 0.5% Decyl Maltoside, 0.5% Dodecyl Sucrose, or 0.5% Tridecyl Maltoside on Blood Glucose Values in Rats

| | Surfactant Agent | | |
|---|---|---|---|
| | Dodecyl Sucrose | Decyl Maltoside | Tridecyl Maltoside |
| Time (min) | Blood Glucose Concentration (mg/dl) | | |
| −20 | 266 | 249 | 255 |
| −10 | 305 | 287 | 307 |
| Insulin eye drops added | | | |
| 0 | 351 | 337 | 323 |
| 10 | 347 | 304 | 309 |
| 20 | 252 | 292 | 217 |
| 30 | 161 | 221 | 131 |
| 40 | 120 | 164 | 100 |
| 50 | 105 | 138 | 87 |
| 60 | 114 | 114 | 107 |
| 70 | 113 | 104 | 115 |
| 80 | 104 | 110 | 79 |
| 90 | 86 | 120 | 85 |
| 100 | 113 | 92 | 76 |
| 110 | 107 | 81 | 74 |
| 120 | 112 | 87 | 75 |
| Glucagon eye drops added | | | |
| 130 | 111 | 95 | 82 |
| 140 | 143 | 99 | 121 |
| 150 | 202 | 132 | 148 |
| 160 | 247 | 157 | 173 |
| 170 | 242 | 171 | 162 |
| 180 | 234 | 180 | 162 |
| 190 | 211 | 189 | 156 |

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A method of increasing absorption of a compound into the circulatory system of a subject comprising administering via the ocular, nasal, nasolacrimal, or inhalation route the compound and an absorption increasing amount of a suitable nontoxic, nonionic alkyl glycoside having a hydrophobic alkyl joined by a linkage to a hydrophilic saccharide.

2. The method of claim 1, wherein the alkyl glycoside has a concentration in the range of about 0.01% to 1.0%.

3. The method of claim 1, wherein the alkyl has from 9 to 24 carbons.

4. The method of claim 3, wherein the alkyl has from 9 to 14 carbon atoms.

5. The method of claim 4, wherein the saccharide is selected from the group consisting of maltose, sucrose and glucose.

6. The method of claim 1, wherein the alkyl glycoside further has a hydrophile-lipophile balance number in the range of about 10 to 20.

7. The method of claim 1, wherein the linkage is selected from the group consisting of a glycosidic linkage, a thioglycosidic linkage, an amide linkage, a ureide linkage and an ester linkage.

8. The method of claim 1, wherein the compound is a protein or a peptide.

9. The method of claim 8, wherein the protein or peptide drug is selected from the group consisting of insulin and glucagon.

10. The method of claim 8, and further comprising administering a protease or peptidase inhibitor.

11. The method of claim 1, wherein the compound is administered in a format selected from the group consisting of a drop, a spray, an aerosol and a sustained-release format.

* * * * *